US007671980B2

(12) United States Patent
Matsui

(10) Patent No.: US 7,671,980 B2
(45) Date of Patent: Mar. 2, 2010

(54) SURFACE INSPECTION METHOD AND SURFACE INSPECTION APPARATUS

(75) Inventor: Shigeru Matsui, Hitachinaka (JP)

(73) Assignee: Hitachi High-Technologies Corporation, Tokyo (JP)

(*) Notice: Subject to any disclaimer, the term of this patent is extended or adjusted under 35 U.S.C. 154(b) by 0 days.

(21) Appl. No.: 12/207,536

(22) Filed: Sep. 10, 2008

(65) Prior Publication Data

US 2009/0284737 A9 Nov. 19, 2009

(30) Foreign Application Priority Data

Sep. 11, 2007 (JP) ............................ 2007-235518

(51) Int. Cl.
*G01N 21/00* (2006.01)

(52) U.S. Cl. ................................ 356/237.3; 356/237.2

(58) Field of Classification Search ............. 356/237.2, 356/237.3, 239.7
See application file for complete search history.

(56) References Cited

U.S. PATENT DOCUMENTS 5,798,829 A * 8/1998 Vaez-Iravani ............ 356/237.1
6,512,578 B1 * 1/2003 Komatsu et al. ......... 356/237.5

FOREIGN PATENT DOCUMENTS

| | | |
|---|---|---|
| JP | 63-036135 A | 2/1968 |
| JP | 2001-255278 | 9/2001 |
| JP | 2002-062479 A | 2/2002 |
| JP | 2002-188999 | 7/2002 |
| JP | 2002-257747 A | 9/2002 |
| JP | 2004-177284 A | 6/2004 |

* cited by examiner

*Primary Examiner*—Roy Punnoose
(74) *Attorney, Agent, or Firm*—Miles & Stockbridge P.C.

(57) ABSTRACT

A surface inspection apparatus capable of acquiring scattered light intensity distribution information for each scattering azimuth angle, and detecting foreign matters and defects with high sensitivity. A concave mirror for condensation and another concave mirror for image formation are used to cope with a broad cubic angle. Since mirrors for condensation and image formation are used, a support for clamping the periphery of a lens is unnecessary, and an effective aperture area does not decrease. A plurality of azimuth-wise detection optical systems is disposed and reflected light at all azimuths can be detected by burying the entire periphery without calling for specific lens polishing. A light signal unification unit sums digital data from a particular system corresponding to a scattering azimuth designated in advance in the systems for improving an S/N ratio.

25 Claims, 9 Drawing Sheets

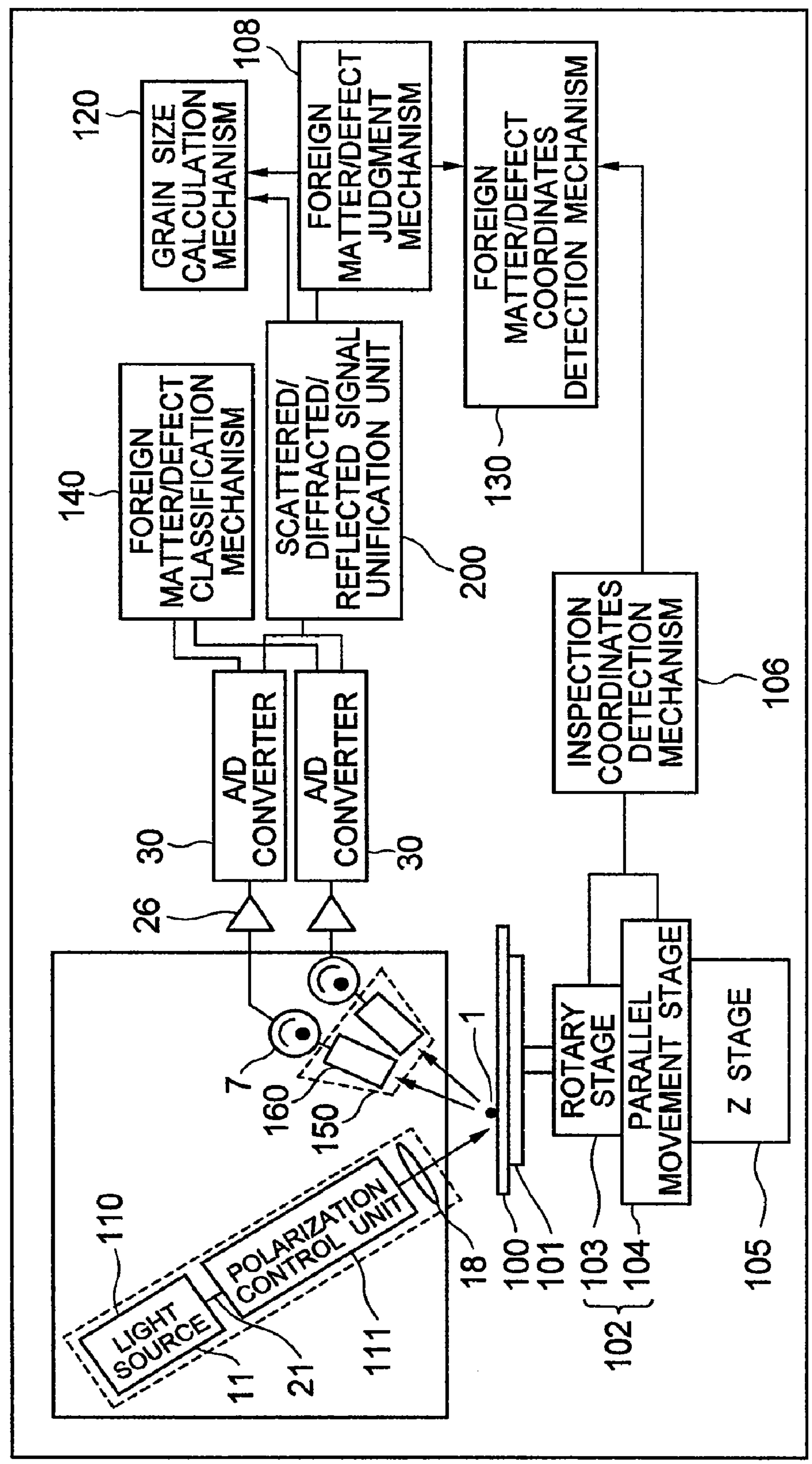
FIG. 1
GRAIN SIZE CALCULATION MECHANISM
120
FOREIGN MATTER/DEFECT JUDGMENT MECHANISM
108
FOREIGN MATTER/DEFECT COORDINATES DETECTION MECHANISM
130
FOREIGN MATTER/DEFECT CLASSIFICATION MECHANISM
140
SCATTERED/ DIFFRACTED/ REFLECTED SIGNAL UNIFICATION UNIT
200
A/D CONVERTER
30
A/D CONVERTER
30
INSPECTION COORDINATES DETECTION MECHANISM
106
26
7
160
150
1
LIGHT SOURCE
POLARIZATION CONTROL UNIT
110
11
21
111
18
100
101
ROTARY STAGE
PARALLEL MOVEMENT STAGE
Z STAGE
103
104
102
105

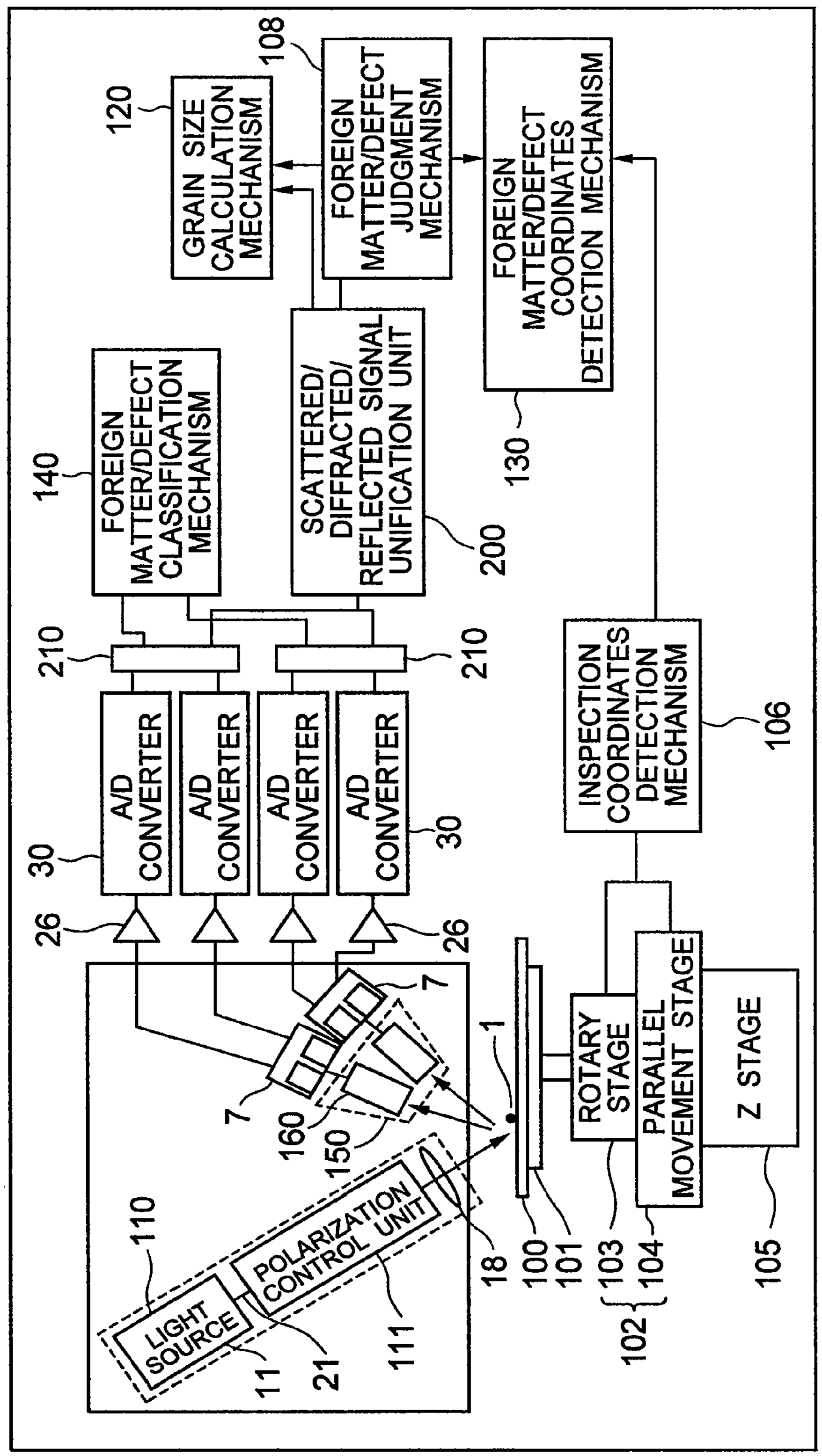
FIG. 9
GRAIN SIZE CALCULATION MECHANISM
120
108
FOREIGN MATTER/DEFECT JUDGMENT MECHANISM
FOREIGN MATTER/DEFECT COORDINATES DETECTION MECHANISM
140
FOREIGN MATTER/DEFECT CLASSIFICATION MECHANISM
SCATTERED/ DIFFRACTED/ REFLECTED SIGNAL UNIFICATION UNIT
200
130
210
210
A/D CONVERTER
A/D CONVERTER
A/D CONVERTER
A/D CONVERTER
30
30
INSPECTION COORDINATES DETECTION MECHANISM
106
26
26
7
7
1
160
150
110
LIGHT SOURCE
POLARIZATION CONTROL UNIT
11
21
111
18
100
101
103
104
102
105
ROTARY STAGE
PARALLEL MOVEMENT STAGE
Z STAGE

SURFACE INSPECTION METHOD AND SURFACE INSPECTION APPARATUS

BACKGROUND OF THE INVENTION

1. Field of the Invention

This invention relates to a surface inspection method, and an apparatus for the method, for inspecting fine foreign matters and defects on a semiconductor substrate (semiconductor wafer).

2. Description of the Related Art

Defect inspection for inspecting foreign matters adhering to a surface of a semiconductor substrate (semiconductor wafer) and scratches occurring during processing has been carried out in a fabrication line of the semiconductor substrate to monitor a occurrence state of dust in production setup. In a semiconductor substrate before the formation of a circuit pattern, for example, fine foreign matters and defects of below dozens of nm must be detected.

In the inspection of the surface of the semiconductor substrate, crystal defects existing in a shallow region in the proximity of the substrate surface and surface coarseness of the substrate surface are also the inspection objects besides the foreign matters and defects.

A customary technology for detecting foreign defects on the surface of the inspection object such as the semiconductor substrate is described in U.S. Pat. No. 5,798,829, for example. This technology fixedly irradiates a condensed laser luminous flux to the surface of the semiconductor substrate, detects scattered light occurring from foreign matters adhering to the semiconductor substrate and inspects the foreign matters and the defects of the entire surface of the semiconductor substrate through rotation and parallel movement of the semiconductor substrate.

A concave mirror using a rotary elliptic surface as a reflecting surface is used for detecting scattered light. The detection position on the semiconductor substrate is set to the first focal point of the ellipsis and a light reception surface of a light reception device is set to the second focal point so that scattered light occurring from the foreign matter can be condensed at a broad cubic angle and fine foreign matters can be detected, too. In this way, the prior art technology does not azimuth-wise isolate and detect scattered light emitted from the foreign matter and defect in all the azimuth directions but collectively condenses and detects the scattered light.

On the other hand, JP-A-2001-255278 discloses a technology that arranges condenser lenses and optical detectors in directions of a plurality of azimuth angles with respect to the surface of a semiconductor substrate and detects scattered light condensed by the condenser lens by an optical detector in accordance with a scattering azimuth. This technology can carry out detection in an advantageous azimuth direction in match with radial direction distribution characteristic of the scattered light from the fine foreign matter.

The technology described in JP-A-2002-188999 detects scattered light from a surface of a semiconductor substrate from all azimuth directions by using one parabolic surface mirror with respect to the surface of the semiconductor substrate.

SUMMARY OF THE INVENTION

However, the surface inspection apparatus of the first patent reference described above that uses the reflecting mirror has the following merits and demerits in comparison with a surface inspection apparatus that isolates, condenses and detects the scattered light from foreign matters and defects in a plurality of azimuth direction by using a condenser lens.

The first merit is that the concave mirror has no break in the azimuth direction (a direction having an axis of symmetry with respect to the normal of the surface of the semiconductor wafer) and continuously bears a condensation operation. From the aspect of a light reception cubic angle, therefore, the concave mirror has no dead angle but has high condensation efficiency.

The second merits resides in that the concave mirror can be supported from the back side by, for example, bonding and fixing a support structure to the back side (not a reflecting surface) and does not hinder condensation efficiency on the reflecting surface side that bears the condensation operation.

The third merit is as follows. Since the foreign matter and defect are detected by condensing and detecting scattered light occurring within a relatively narrow range of the angle of elevation by using one optical detector, the number of photons that are incident into one optical detector can be advantageously secured. Particularly, when the foreign matter and defect as the detection object is extremely small and the resulting total scattered light quantity is markedly small, a satisfactory S/N ratio can be secured.

On the other hand, the first demerit is that scattered light intensity distribution information cannot be obtained for each scattering azimuth direction and classification capacity of the detected foreign matter and defect is inferior.

The second demerit is that since only background scattered light that becomes noise from an azimuth direction in which scattered light from the foreign matter and defect is weak is summed for those foreign matters and defects which have strong scattered light distribution in a specific azimuth direction, the S/N ratio is not satisfactory.

The surface inspection apparatus described in the second patent reference that uses a plurality of condenser lenses has the following merits and demerits in comparison with the surface inspection apparatus that collectively condenses scattered light from the foreign matters and defects by using one concave mirror using a rotary elliptic surface as a reflecting surface.

The first merit is that classification capacity of the detected foreign matter and defect is high because scattered light intensity distribution information for each scattering azimuth angle can be acquired.

The second merit is as follows. It is possible not to pick up only those background scattered light which may result in the noise in the azimuth direction in which scattered light is weak for the foreign matter and defect having a strong scattered light distribution in only a specific azimuth direction. (It is advisable not to use a signal in such an azimuth direction). This is advantageous in the aspect of the S/N ratio.

On the other hand, the first demerit is as follows. Because the range of an azimuth angle of 360 degrees of the entire periphery having a substantially equal angle of elevation must be covered with a plurality of lens incidence surfaces, a plurality of lenses are arranged in alignment on the circumference that has a predetermined radius. To bury the entire periphery without gaps, the shape of the incidence surface of the individual lens must be polished into a shape approximate to a rectangle or a trapezoid.

The second demerit is that a frame-like support structure is necessary for clamping and holding the lenses from their periphery and the effective aperture area bearing the condensation operation becomes smaller as much.

The third demerit is that when the foreign matter and defect as the detection object is extremely small and the resulting total scattered light quantity is markedly small, the number of photons incident into one optical detector decreases extremely when the total scattered light quantity is divided into a plurality of azimuths. This is disadvantageous from the aspect of the S/N ratio.

The technology described in the third patent reference mentioned above involves the problem that the S/N ratio drops when the foreign matter and defect as the inspection object is extremely small and the resulting scattered light quantity is markedly small.

The surface inspection apparatus in the latest semiconductor device fabrication process is required to be capable of detecting and classifying a greater number of kinds of foreign matters and defects as the minimum detection grain size of the foreign matters and defects has become smaller.

To satisfy such a requirement, a condensation optical system capable of conducting detection in a plurality of azimuths and improving detection sensitivity has been required.

It is an object of the invention to accomplish a surface inspection method and a surface inspection apparatus each being capable of acquiring scattered light intensity distribution information for each scattering azimuth and detecting foreign matters and defects with high sensitivity.

To accomplish the object, the invention employs the following construction.

A surface inspection method according to the invention irradiates light to a predetermined position on a surface of an inspection object to form an illumination spot, detects light that is scattered, diffracted and reflected from the illumination spot and detects foreign matters and defects existing on the surface of the inspection object or in the proximity of, and inside, the surface on the basis of light detected.

The light scattered, diffracted and reflected from the illumination spot is condensed and reflected by a plurality of concave mirrors for condensation that are arranged for each of a plurality of azimuth angles with respect to the surface of the inspection object, reflects light reflected from the condensation concave mirrors arranged at the same azimuth angle by concave mirrors for image formation that are arranged at a higher angle of elevation than the condensation concave mirrors with respect to the surface of the inspection object, distinguishes and detects the light reflected from the plurality of image formation concave mirrors, respectively at a detection device, and detects the foreign matters and defects existing on the surface of the inspection object or in the proximity of, and inside, the surface on the basis of the light detected.

A surface inspection apparatus according to the invention includes an inspection object movement stage on which an inspection object is put and which moves the inspection object, illumination device that irradiates light to a predetermined position on a surface of the inspection object and forming an illumination spot, and detection device that detects light scattered, diffracted and reflected from the illumination spot, and detects the foreign matters and defects existing on the surface of the inspection object or in the proximity of, and inside, the surface on the basis of light detected by the detection device.

The surface inspection apparatus further includes a plurality of condensation concave mirrors arranged at a plurality of azimuth angles, respectively, with respect to the surface of the inspection object, and condensing and reflecting light scattered, diffracted and reflected from the illumination spot; image formation concave mirrors arranged at a higher angle of elevation than the condensation concave mirror with respect to the surface of the inspection object at each of the plurality of azimuth angles, and reflecting light reflected from the condensation concave mirrors arranged at the same azimuth angles; another detection device that distinguishes and detects each of the rays of light reflected by the plurality of image formation mirrors; and foreign matter/defect classification device that detects the foreign matters and defects existing on the surface of the inspection object or in the proximity of, and inside, the surface on the basis of light detected by the detection device.

The invention can accomplish a surface inspection method, and an apparatus for the method, each capable of acquiring scattered light intensity distribution information for each scattering azimuth and detecting foreign matters and defects with high sensitivity.

BRIEF DESCRIPTION OF THE DRAWINGS

FIG. 1 is a schematic structural view of a surface inspection apparatus for executing a surface inspection method according to a first embodiment of the present invention;

FIG. 9 is a schematic structural view of a surface inspection apparatus for executing a surface inspection method according to the second embodiment of the invention.

DESCRIPTION OF THE EMBODIMENTS

Figure 2:
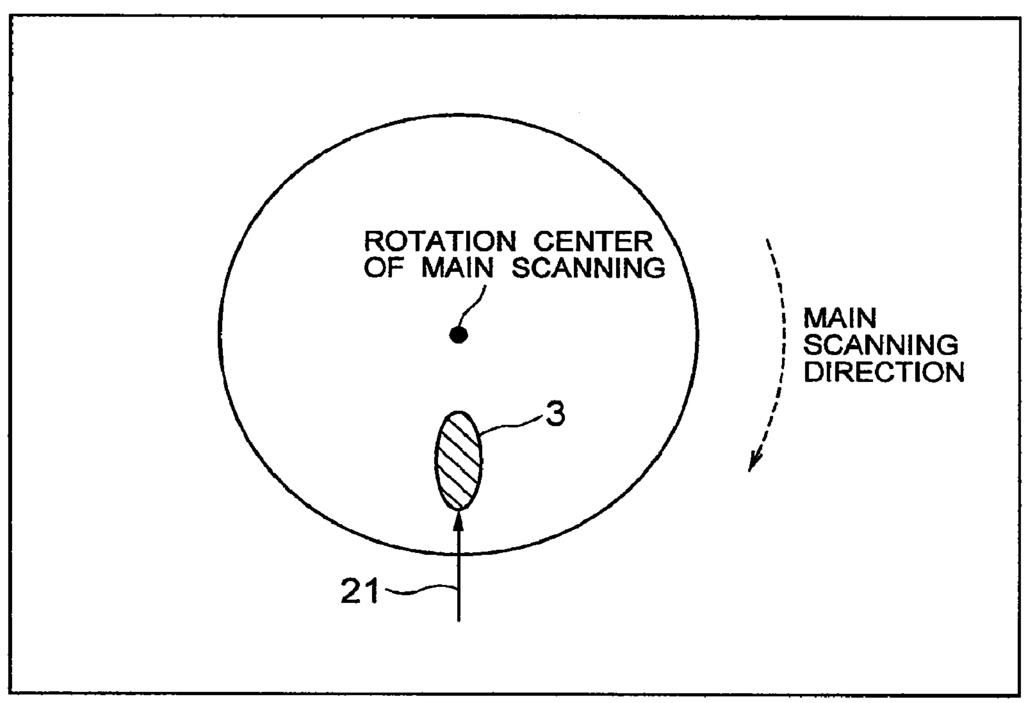
FIG. 2 is an explanatory view useful for explaining an illumination spot in the first embodiment of the invention.

Preferred embodiments of the invention will be hereinafter explained with reference to the accompanying drawings.

FIG. 1 is a schematic structural view of a surface inspection apparatus for executing a surface inspection method according to a first embodiment of the present invention. In the drawing, a semiconductor wafer 100 as an inspection object is shown adsorbed by vacuum to a chuck 101. The chuck 101 is mounted onto an inspection object movement stage 102 having a rotation stage 103, a parallel movement stage 104 and a Z stage 105.

An illumination optical system 110 and a scattered/diffracted/reflected light detection optical system 150 are arranged above the semiconductor wafer 100. A pulse laser that causes time-wise repeatedly pulse oscillation of light of a wavelength of the ultraviolet region is used for a light source 11. An illumination beam 21 outgoing from the light source 11 forms an illumination spot 3 shown in FIG. 2 owing to the operation of an illumination lens 18. To detect highly precisely fine foreign matters and defects, an angle of elevation of the illumination beam 21 to the surface of the inspection object is a low angle of elevation of about 5 to about 25 degrees, more preferably an angle in the proximity of the Brewster angle with respect to the material constituting the inspection object, such as crystalline Si (silicon).

In the first embodiment of the invention, therefore, the illumination beam 21 is allowed to be incident obliquely at an angle of about 13 degrees. For this reason, the illumination spot 3 has a substantially elliptic shape. The polarization state of the illumination beam 21 is controlled to "P polarization" or "S polarization" or "circular polarization" or "elliptic polarization".

Scattered/diffracted/reflected light generated from the illumination spot 3 is condensed and detected by the scattered/diffracted/reflected light detection optical system 150. The scattered/diffracted/reflected light detection optical system 150 has six azimuth-wise detection optical systems 160 the detection direction angles of which are spaced apart from one another by about 60 degrees so that the components scattered, diffracted and reflected in directions of left front/right front/left side/right side/left back/right back among the scattered/diffracted/reflected light generated from the illumination spot 3 by the illumination beam 21 can be isolated and detected individually.

Figure 3:
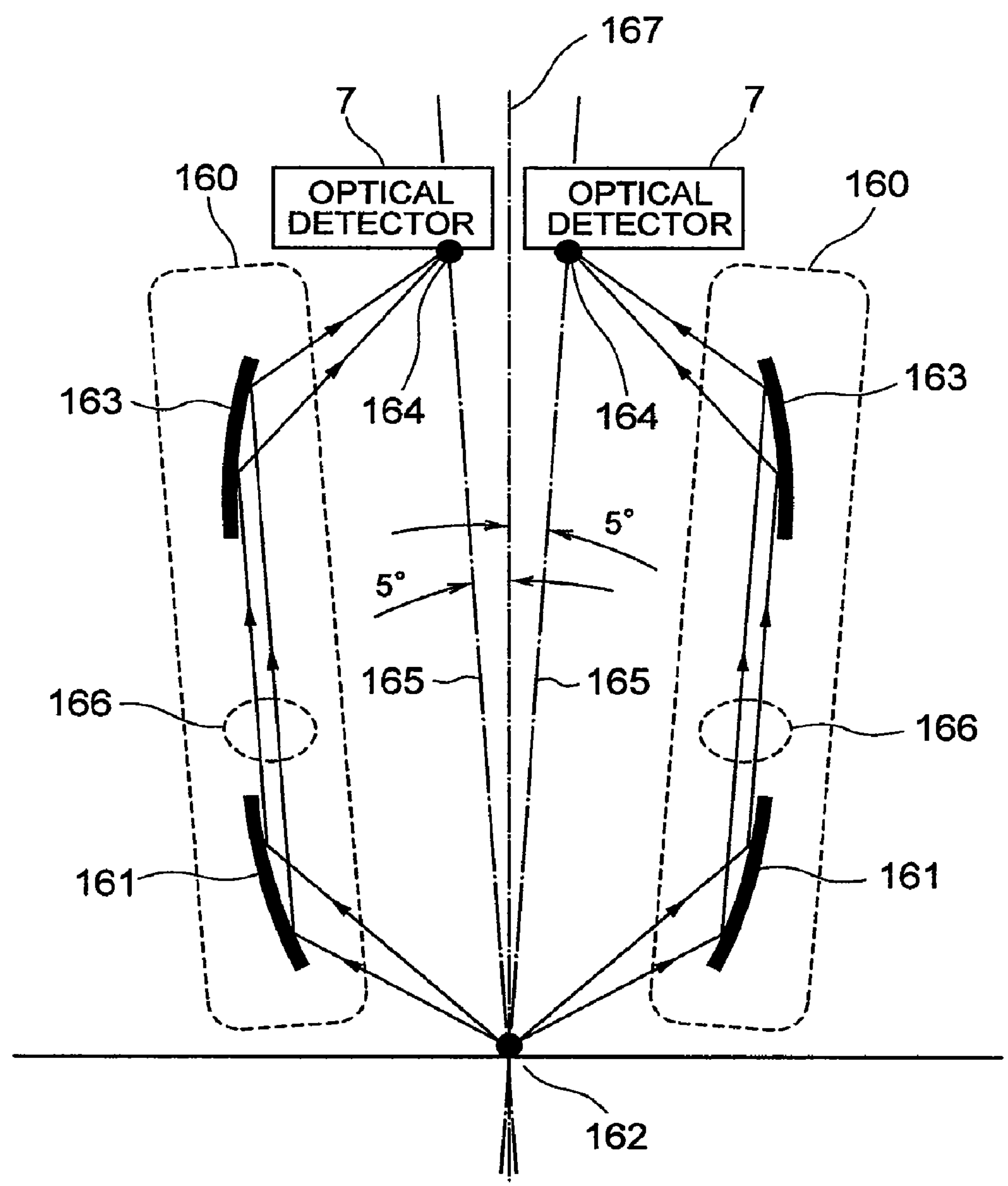
FIG. 3 is an explanatory view useful for explaining an azimuth-wise detection optical system in the first embodiment of the invention.
Figure 4:
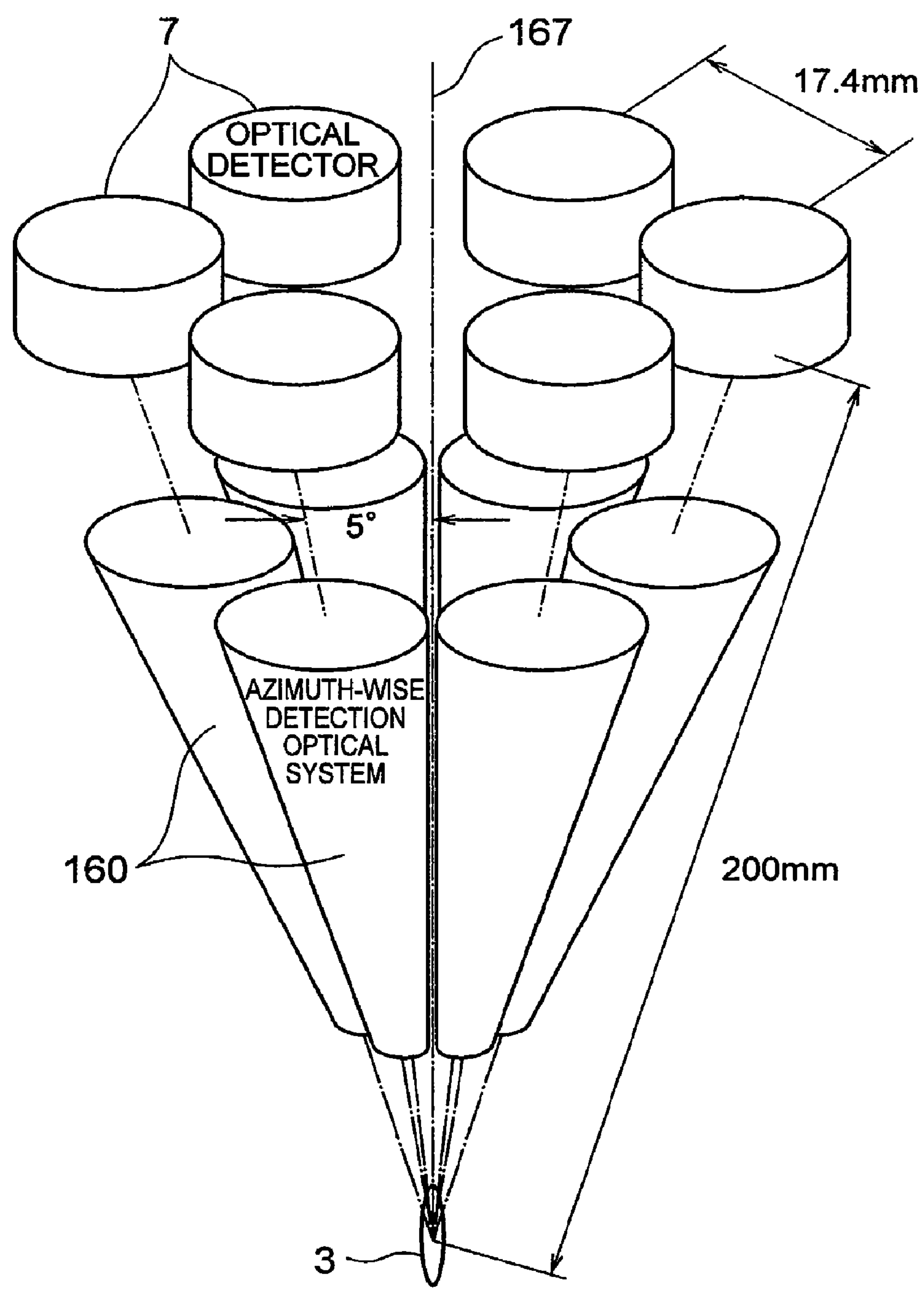
FIG. 4 is an explanatory view useful for explaining an arrangement of optical detectors in the first embodiment of the invention.

FIG. 3 is a schematic structural view of each azimuth-wise detection optical system 160. As described above, the concave mirror using a rotary elliptic surface as a reflecting surface can condense light emission dispersed in a broad cubic angle range from near a first focal point by only a single reflecting surface but cannot form images of two light emission points existing in the proximity of the first focal point as separate images of two points in the proximity of a second focal point. A combination of at least two secondary curved surface concave mirrors is necessary to constitute an optical system having an image formation capacity while suppressing spherical aberration and astigmatism by only a reflecting mirror using its secondary curved surface as a reflecting surface.

Combinations of a rotary double curved surface+rotary double curved surface, rotary curved surface+rotary elliptic surface and rotary double curved surface+paraboloid of revolution have already been put into practical application in the field of astronomical microscopes using visible rays and X rays but a cubic angle range capable of condensation is narrow. Scattered light scattering in a broad cubic angle from foreign matters and defects must be received in optical surface inspection, and the condensation cubic angle capable of being achieved by the combinations described above has not been entirely satisfactory. The combination of the paraboloid of revolution+paraboloid of revolution is one of the combinations capable of coping with a broad cubic angle among the combinations for achieving the image formation capacity by two secondary curved surface concave mirrors.

In the first embodiment of the invention, therefore, the azimuth-wise detection optical system 160 includes a concave mirror 161 for condensation that uses a part of its paraboloid of revolution as a reflecting surface and a concave mirror 163 for image formation that uses a part of its paraboloid of revolution as a reflecting surface. The paraboloid of revolution of the reflecting surface of the condensation concave mirror 161 and the paraboloid of revolution of the reflecting surface of the image formation concave mirror 163 have a common optical axis 165. The common optical axis 165 is inclined outward by about 5 degrees to the normal 167 of the surface of the inspection object in the detection direction to which the azimuth-wise detection optical system 160 corresponds, as shown in FIG. 3.

The focus 162 of the paraboloid of revolution of the reflecting surface of the condensation concave mirror 161 is arranged substantially in conformity with the center of the illumination spot 3 on the surface of the inspection object and the focus 164 of the paraboloid of revolution of the reflecting surface of the condensation concave mirror 163 is arranged substantially in conformity with the center of the light reception surface of the optical detector 7. The focal length of the condensation concave mirror 161 is set to be substantially equal to that of the image formation concave mirror 163.

In the arrangement described above, the scattered/diffracted/reflected light occurring from the illumination spot 3 is converted to a parallel pencil of rays 166 by the condensation concave mirror 161 and these rays are incident into the image formation concave mirror 163. The image formation concave mirror 163 forms the image of the parallel pencil of rays 166 on the optical detector 7 as the focal surface and forms the image that is substantially a multiple of the illumination spot. In the first embodiment of the invention, the distance from the focus 162 of the condensation concave mirror 161 to the focus 164 of the image formation concave mirror 163, that is to say, the distance from the center of the illumination spot 3 to the center of the light reception surface of the optical detector 3, is set to about 200 mm.

Therefore, when the common optical axis 165 of the condensation concave mirror 161 and the image formation concave mirror 165 is inclined by about 5 degrees to the normal 167 of the surface of the inspection object, the gap between the images of the adjacent measurement spots 3 corresponds to the length of one side of an equilateral hexagon inscribed in a circle the radius of which satisfies the relation 200 mm×sin 5°=approx. 17.4 mm (formula 1). Therefore, the gap between the images of the adjacent measurement spots 3, too, is 17.4 mm and the illumination spot image formed by each of the six azimuth-wise detection optical systems 160 does not spatially interfere with one another but can be isolated and detected by the independent optical detector 7 that is disposed for each azimuth-wise detection optical system.

Figure 5A:
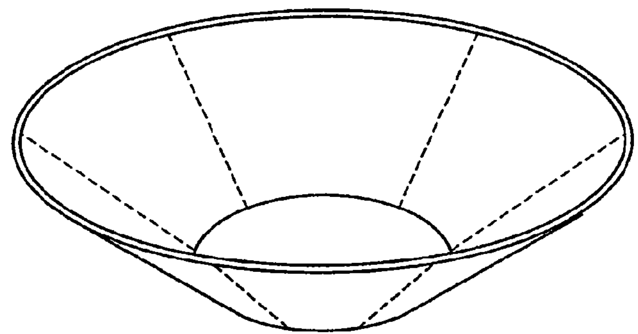
FIGS. 5A to 5C are explanatory views each useful for explaining a concave mirror for condensation in the first embodiment of the invention.
Figure 5B:
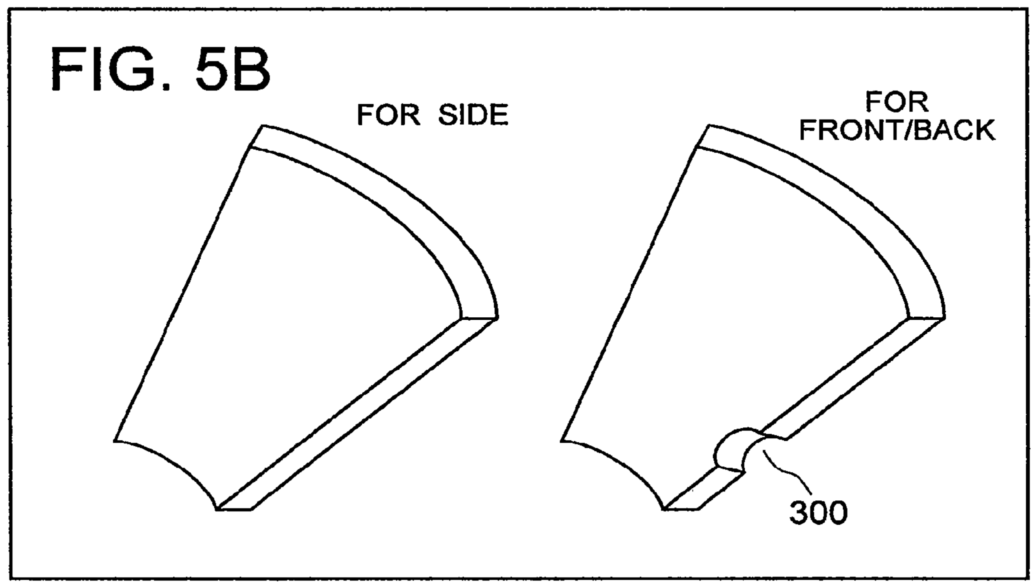
Figure 5C:
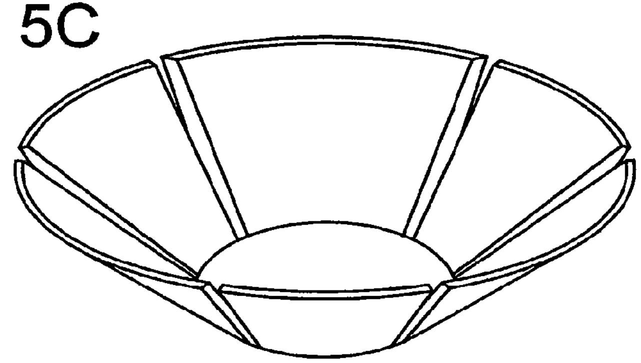

As shown in FIG. 5A, six, in total, of condensation concave mirrors 161 of the six azimuth-wise detection optical systems 160 are produced by splitting one rotary elliptic surface mirror into six units. The outer shape of the reflecting surface of each condensation concave mirror 161 is such as shown in FIG. 5B. Four condensation concave mirrors 161, that is, the left front/right front/left back/right back concave mirrors, have a small semi-spherical notch portion 300 to avoid the illumination beam 21 and the optical path of the regular reflected light of the illumination beam 21. These six condensation concave mirrors 161 are arranged in such a fashion that the gap between the adjacent pair of condensation concave mirrors 161 becomes small as shown in FIG. 5C.

As described above, in the first embodiment of the invention, the angle of elevation of irradiation of the illumination beam 21 is set to 13 degrees. It is known that in the case of foreign matters satisfying the Rayleigh scattering rule, scattered light from the foreign matters mostly occurs within the range of the angle of elevation of about 7 to about 50 degrees.

The arrangement according to the first embodiment of the invention can efficiently condense and detect those types of light which are scattered, diffracted and reflected within the range of the angle of elevation of about 7 to about 50 degrees among the scattered, diffracted and reflected light occurring from the illumination spot 3.

When the foreign matter 1 passes by the illumination spot 3 in the construction described above, the scattered/diffracted/reflected signal can be obtained from the optical detector corresponding to each azimuth-wise detection optical system 160. The first embodiment of the invention uses a photomultiplier for the optical detector 7 but optical detectors based on other detection principles may be used, too, as long as they can detect with high sensitivity the scattered/diffracted/reflected light from the foreign matter.

The scattered/diffracted/reflected light signal from each optical detector is amplified by the amplifier 26 disposed for each optical detector 7, is sampled in a predetermined sampling cycle dT and is converted to digital data by an A/D converter 30. The group of the digital data acquired in such a fashion as to correspond to each azimuth-wise detection optical system 160 is sent to a scattered/diffracted/reflected signal unification unit 200. The scattered/diffracted/reflected signal unification unit 200 sums the digital data from the azimuth-wise detection optical system 160 corresponding to a predetermined scattering direction and can thus accomplish data processing for acquiring unified digital data having an S/N ratio which is much more improved than an S/N ratio obtained by the mere addition of the digital data. Weighted linear coupling may be used for the synthetic algorithm of these digital data.

The unified digital data obtained by the scattered/diffracted/reflected signal unification unit 200 is thereafter compared with a detection threshold value that is determined in advance by a foreign matter/defect judgment mechanism 108. The foreign matter/defect judgment mechanism 108 judges that the digital data originates from the foreign matter and defect when the digital data is greater than the threshold value and generates the foreign matter/defect judgment information. When the foreign matter/defect judgment information is supplied from the foreign matter/defect judgment mechanism 108, a foreign matter/defect coordinate detection mechanism 130 calculates the coordinate position (r, θ) of the foreign matter and defect in a main scanning direction and in a sub-scanning direction from the positional information of the present position of main scanning and sub-scanning that are generated by the inspection object movement stage 102. When the coordinate position of the detected foreign matter and defect is determined, a grain size calculation mechanism 120 subsequently calculates the size of the detected foreign matter and defect from the digital data group.

On the other hand, the digital data group so obtained as to correspond to each azimuth-wise detection optical system 160 is sent to the scattered/diffracted/reflected light signal unification unit 200 and at the same time is sent to a foreign matter/defect classification mechanism 140, too, in the form of individual digital data. The foreign matter/defect classification mechanism 140 compares the intensities of the digital data of the scattering direction and judges to which of a predetermined foreign matter/defect category the detected foreign matter and defect corresponds.

As described above, the first embodiment of the invention can cope with a broad cubic angle by means of the condensation concave mirror 161 using a part of its paraboloid of revolution as the reflecting surface and the image formation concave mirror 163 using a part of its paraboloid of revolution as the reflecting surface.

Since the first embodiment uses the condensation concave mirror 161 and the image formation concave mirror 163 as the reflecting mirror, a support for holding a lens by clamping its periphery like a condenser lens is not necessary and an effective aperture area does not become small.

Since the embodiment uses the conical reflecting mirrors, that is, a plurality of azimuth-wise detection optical systems produced by dividing a paraboloid of revolution mirror, the embodiment can detect reflected light in all azimuth directions by burying the whole periphery without any gap and without calling for specific lens polishing.

Since the scattered/diffracted/reflected light signal unification unit 200 sums the digital data from the azimuth-wise detection optical system 160 corresponding to the scattering direction designated in advance among a plurality of azimuth-wise detection optical systems 160, the S/N ratio can be much more improved than the S/N ratio obtained by mere addition of the data from all the azimuth-wise detection optical systems 160.

In other words, the first embodiment of the invention makes it possible to conduct the following three (1) to (3).

(1) to acquire scattered light intensity distribution information at each scattering azimuth angle;

(2) to separate and utilize the scattered light signal from a scattering azimuth direction advantageous for the S/N ratio; and (3) A dead angle is small at all azimuth directions and in a necessary range of angle of elevation at light reception cubic angles of the condensation optical system and condensation efficiency is high.

The explanation given above primarily deals with the detection of foreign matters and defects but it would be obvious that the similar effect can be obtained when surface coarseness of the semiconductor wafer 100 as the inspection object is measured, too.

In the first embodiment described above, the light source 11 is the "pulse laser causing time-wise repeatedly the pulse oscillation of light of the wavelength of the ultraviolet region" but lasers of the wavelengths other than the ultraviolet region may be used, too. When the continuously oscillating laser is used for the light source, too, the technology described above can be as such adapted. In the first embodiment described above, the number of directions for isolating and detecting the scattered/diffracted/reflected light occurring from the foreign matter and defect are the six directions of the left front/right front/left side/right side/left back/right back and the six azimuth-wise detection optical systems 160 the detection direction angles of which are spaced apart from one another by about 60 degrees are arranged. However, the merit of the azimuth-wise isolation and detection can be enjoyed when at least four directions of the front/left side/right side/back can be detected.

In the embodiment described above, further, the focal length of the condensation concave mirror 161 is set to be substantially equal to the focal length of the image formation concave mirror 163 so as to form an image having substantially an equal size to the illumination spot but a focal length different from that of the condensation concave mirror 161 may be given to the image formation concave mirror 163 so as to form an enlarged image of the illumination spot.

Incidentally, when the foreign matter and defect as the detection object is extremely small and the resulting total scattered light quantity is markedly small, the number of photons incident into one optical detector 7 drastically decreases if the total scattered light quantity is to be divided and detected by a plurality of azimuth-wise detection optical systems 160. In such a case, it may be more advantages from the aspect of the S/N ratio to guide the total scattered light quantity into the single optical detector without isolation.

Figure 6:
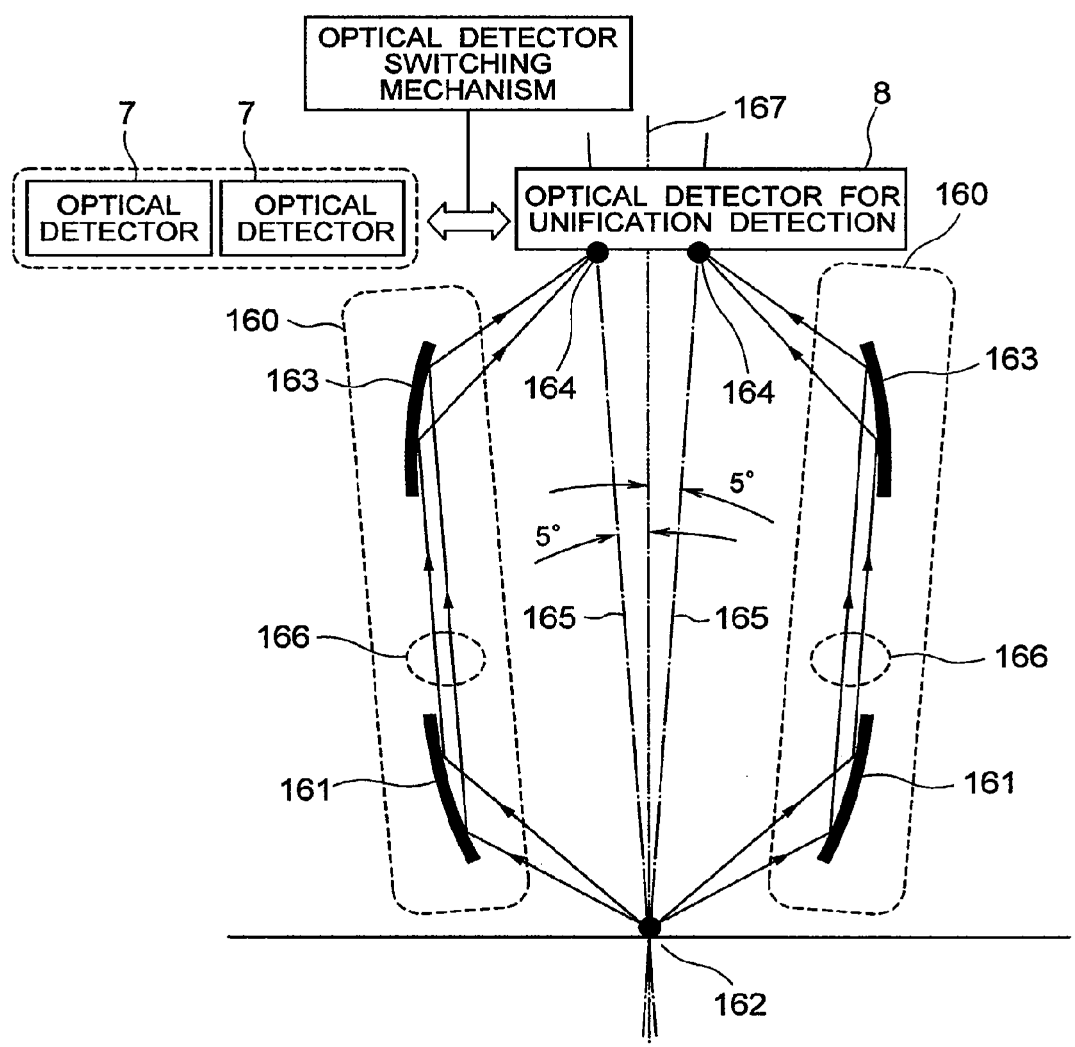
FIG. 6 is an explanatory view useful for explaining another arrangement of the optical detectors in the first embodiment of the invention.

In such a case, an optical detector 8 for unified detection is disposed in addition to the optical detectors 7 corresponding to the respective azimuth-wise detection optical system 160 as shown in FIG. 6 so that the optical detector 8 for unified detection and a plurality of optical detectors 7 can be changeably utilized.

An optical detector the light reception surface of which is greater than the circle having the radius given by the aforementioned formula 1 such as a head-on type photomultiplier having a large aperture is suitable for the optical detector 8 for unified defection. When the optical detector is constituted in this way, the first embodiment of the invention makes it possible "(4) to secure the number of photons incident into one optical detector even when the foreign matter and defect as the detection object is extremely small and the resulting total scattered light quantity is markedly small", too.

In the first embodiment of the invention described above, the number of illumination spots formed on the surface of the inspection object is 1 but it is also possible to employ the construction in which a plurality of illumination spots are formed and scattered/diffracted/reflected light from each illumination spot is individually detected.

Figure 7:
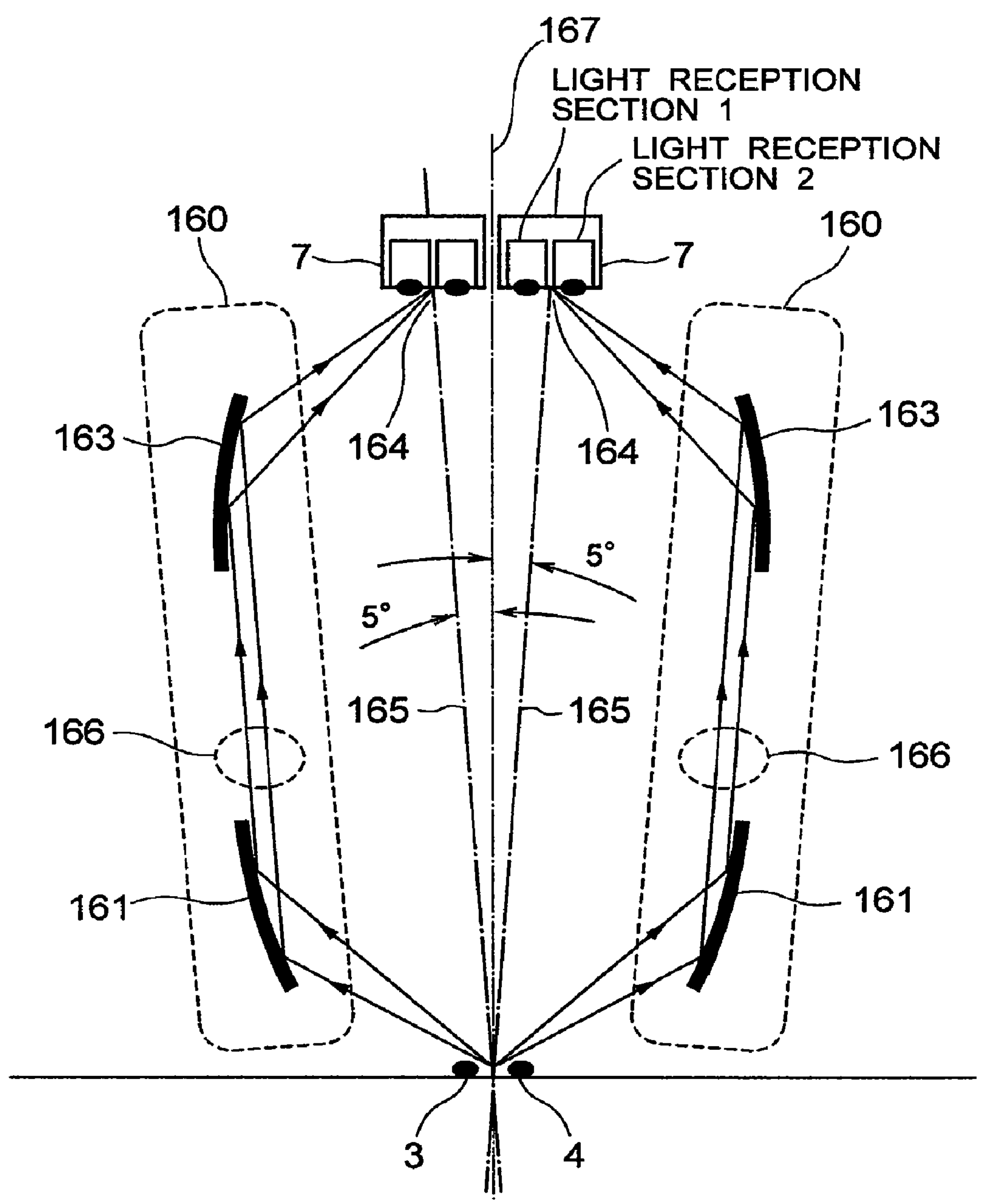
FIG. 7 is an explanatory view useful for explaining a condensation/detection optical system of a surface inspection apparatus according to a second embodiment of the invention.

FIG. 7 shows a condensation/detection optical system according to the second embodiment that individually detects scattered/diffracted/reflected light occurring from a plurality of illumination spots.

It is possible to split light leaving a single light source into a plurality of illumination beams and to form a plurality of illumination spots by a technology using a beam splitter or a technology using a Wollaston polarizing prism for an illumination optical system.

Figure 8:
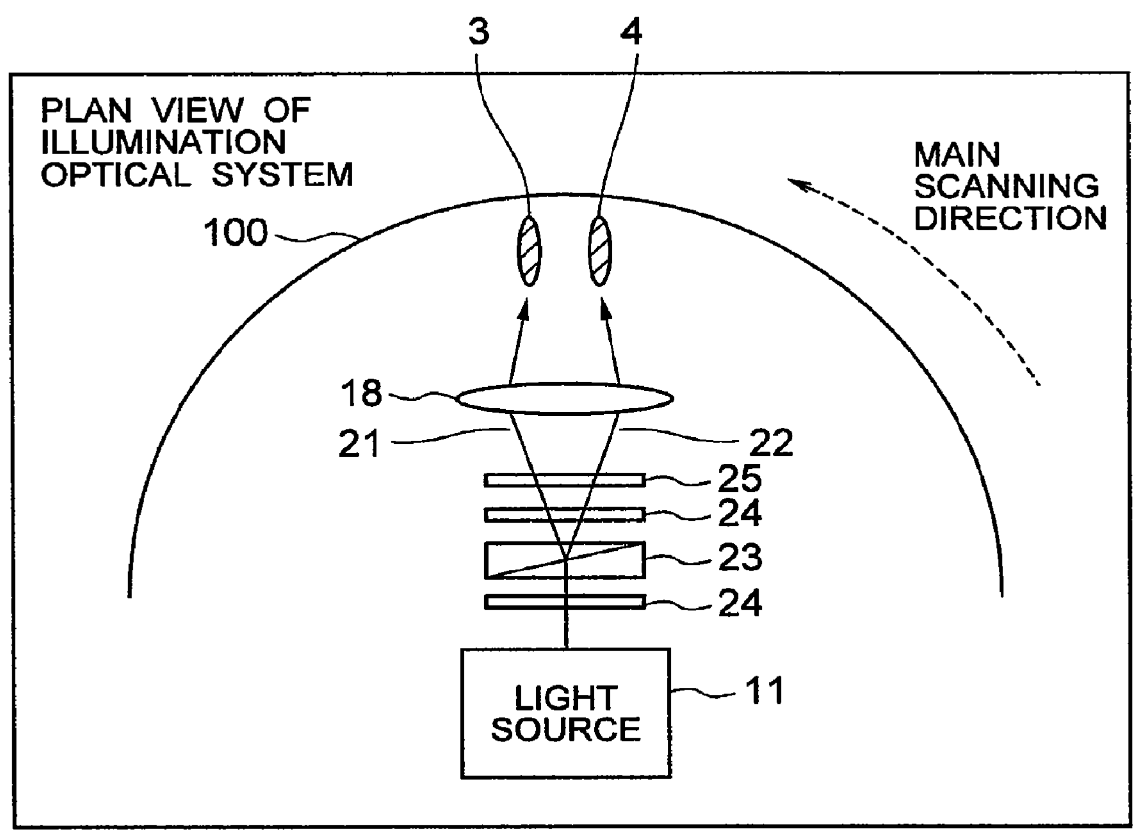
FIG. 8 is an explanatory view useful for explaining the formation of an illumination spot in the second embodiment of the invention.

FIG. 8 shows a construction in which light is split into two illumination beams by the Wollaston polarizing prism 23 and two illumination spots 3 and 4 are formed on a semiconductor wafer 100 by the operation of an illumination lens 18.

FIG. 9 is a schematic structural view of a surface inspection apparatus for executing a surface inspection method according to the second embodiment of the invention.

The intensity ratio of the two illumination spots 3 and 4 and their polarization state can be adjusted by setting angles of a polarizer 24 and a ½ wavelength plate 25. The constructions and condensation/image formation of the scattered/diffracted/reflected light detection optical system 150 and the six azimuth-wise detection optical systems 160 are the same as those of the first embodiment described above. Therefore, explanation will be omitted.

In the second embodiment of the invention, each azimuth-wise detection optical system 160 forms the images of two illumination spots 3 and 4. An optical detector having two light reception sections is used for the optical detector 7 provided to each azimuth-wise detection optical system 160 and each light reception partition can detect one illumination spot image.

The common optical axis 165 of the condensation concave mirror 161 and the image formation concave mirror 163 constituting each azimuth-wise detection optical system 160 is inclined outward by about 5 degrees to the normal 167 of the surface of the inspection object in the detection direction to which each azimuth-wise detection optical system 160 corresponds. Therefore, a point deviated from the optical axis 165 on the surface of the inspection object in the images of the illumination spots 3 and 4 has aberration.

To reduce this aberration, the line connecting the centers of the two light reception sections in the optical detector 7 is arranged in such a fashion as to be inclined with respect to the optical axis 165 but not orthogonal. Because the output signals can be obtained in parallel with each other from the two light reception sections, each optical detector 7 is connected to two amplifiers 26 and two A/D converters 30.

The digital data obtained from the two A/D converters 30 are synthesized by a plural illumination signal unification units 210. When the intensity of the two illumination spots 3 and 4 is set to be equal to each other by angle setting of the polarizer 24 and the ½ wavelength plate 25, the S/N ratio can be improved by $\sqrt{2}$ times by calculating addition mean of the two signals of the illumination spots 3 and 4 by the plural illumination spot signal unification unit 210 in comparison with the case where a single optical detector having the same detection sensitivity and the same noise characteristics is used.

The output digital data of this plural illumination spot signal unification unit 210 is sent to the scattered/diffracted/reflected signal unification unit 200. Since the subsequent functions and operations of the scattered/diffracted/reflected signal unification unit 200 are the same as those of the first embodiment, explanation in detail will be omitted.

In addition to the advantages (1) to (4) obtained in the first embodiment, the second embodiment provides the advantage that a higher S/N ratio can be obtained by disposing the detector capable of forming a plurality of illumination spots, isolating them, forming their images and detecting them individually to average a plurality of scattered/diffracted/reflected light signals.

As described above, the invention provides the effects listed below by using a plurality of azimuth-wise detection optical systems each acquiring the image formation operation by a pair of two concave mirrors using its paraboloid of revolution as the reflecting mirror.

(1) It is possible to acquire scattered light intensity distribution information for each scattering direction angle.

(2) The scattered light signal from the scattering direction angle that is advantages from the aspect of the S/N ratio can be isolated and utilized.

(3) The dead angles are small for all azimuth angles and within the required range of the angle of elevation in the reception light cubic angles of the condensation optical system and condensation efficiency is high.

(4) Even when the foreign matter and defect as the detection object is extremely small and the resulting total scattered light quantity is markedly small, the number of photons incident into one optical detector can be secured.

The invention can be established not only as the surface inspection method and apparatus for semiconductor wafers, etc, but also as an azimuth-wise scattered light image formation optical apparatus for a surface inspection apparatus having a scattered/diffracted/reflected light detection optical system 150 and a detector 7.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A surface inspection method by irradiating light to a predetermined position on a surface of an inspection object to form an illumination spot, detecting light scattered, diffracted and reflected from said illumination spot, and detecting foreign matters and defects existing on the surface of said inspection object or in the proximity of, and inside, the surface, said method comprising the steps of:

condensing and reflecting the light scattered, diffracted and reflected from said illumination spot by a plurality of condensation concave mirrors arranged at a plurality of azimuth angles with respect to the surface of said inspection object, respectively;

reflecting light reflected from each of said condensation concave mirrors arranged at a predetermined positional relationships with each of a plurality of image formation concave mirrors arranged at a higher angle of elevation than said condensation concave mirror with respect to the surface of said inspection object for each of said plurality of azimuth angles;

distinguishing and detecting light reflected by said plurality of image formation concave mirrors; and detecting foreign matters and defects existing on the surface of said inspection object or in the proximity of, and inside, the surface of said inspection object on the basis of the light detected.

2. A surface inspection method according to claim 1, wherein the light reflecting surface of each of said condensation concave mirrors is a paraboloid of revolution or a part of the paraboloid of revolution.

3. A surface inspection method according to claim 2, wherein said plurality of condensation concave mirrors is produced by splitting one paraboloid of revolution mirror.

4. A surface inspection method according to claim 3, wherein the light reflecting surface of each of said image formation concave mirrors is a paraboloid of revolution or a part of the paraboloid of revolution.

5. A surface inspection method according to claim 4, wherein each of said condensation concave mirrors and each of said image formation concave mirrors execute image formation at a substantially equal magnification.

6. A surface inspection method according to claim 4, wherein each of said condensation concave mirrors and each of said image formation concave mirrors execute magnification image formation.

7. A surface inspection method according to claim 4, wherein each of said condensation concave mirrors and each of said image formation concave mirrors are arranged in such a fashion that an optical axis of the paraboloid of revolution of one of said condensation concave mirrors and an optical axis of the paraboloid of revolution of one of said image formation concave mirrors corresponding to the one of said condensation concave mirrors has a common optical axis, and said common optical axis is inclined in said azimuth direction with respect to a normal of the surface of said inspection object.

8. A surface inspection method according to claim 7, wherein said common optical axis is inclined at an angle of about 5 to about 45 degrees in said azimuth direction with respect to the normal of the surface of said inspection object.

9. A surface inspection method according to claim 1, wherein each of images of said illumination spot formed for each azimuth is individually detected by a plurality of optical detectors or an optical detector having a plurality of light reception sections, and is converted to an electric signal.

10. A surface inspection method according to claim 1, wherein the predetermined positional relationship comprises the same azimuth angle.

11. A surface inspection apparatus for detecting foreign matters and defects existing on a surface of an inspection object or in the proximity of, and inside, the surface, on the basis of light detected by a detection device, including an inspection object movement stage on which an inspection object is put and which moves said inspection object, illumination device that irradiates light to a predetermined position on a surface of said inspection object and forming an illumination spot, and said detection device that detects light scattered, diffracted and reflected from said illumination spot, comprising:

a plurality of condensation concave mirrors arranged at a plurality of azimuth angles, respectively, with respect to the surface of said inspection object, and condensing and reflecting light scattered, diffracted and reflected from said illumination spot;

a plurality of image formation concave mirrors arranged at a higher angle of elevation than said condensation concave mirror with respect to the surface of said inspection object at each of said plurality of azimuth angles, and reflecting light reflected from each of said condensation concave mirrors arranged at a predetermined positional relationships with each of the plurality of image formation concave mirrors;

another detection device that distinguishes and detects each of the rays of light reflected by said plurality of image formation mirrors; and foreign matter/defect classification device that detects foreign matters and defects existing on the surface of said inspection object or in the proximity of, and inside, the surface on the basis of light detected by said detection device.

12. A surface inspection apparatus according to claim 11, wherein the light reflecting surface of each of said condensation concave mirrors is a paraboloid of revolution or a part of the paraboloid of revolution.

13. A surface inspection apparatus according to claim 12, wherein said plurality of condensation concave mirrors is produced by splitting one paraboloid of revolution mirror.

14. A surface inspection apparatus according to claim 13, wherein the light reflecting surface of each of said image formation concave mirrors is a paraboloid of revolution or a part of the paraboloid of revolution.

15. A surface inspection apparatus according to claim 14, wherein each of said condensation concave mirrors and each of said image formation concave mirrors execute image formation at a substantially equal magnification.

16. A surface inspection apparatus according to claim 14, wherein each of said condensation concave mirrors and each of said image formation concave mirrors execute magnification image formation.

17. A surface inspection apparatus according to claim 14, wherein each of said condensation concave mirrors and each of said image formation concave mirrors are arranged in such a fashion that an optical axis of the paraboloid of revolution of each of said condensation concave mirrors and an optical axis of the paraboloid of revolution of said image formation concave mirror have a common optical axis, and said common optical axis is inclined in said azimuth direction with respect to a normal of the surface of said inspection object.

18. A surface inspection apparatus according to claim 17, wherein said common optical axis is inclined at an angle of about 5 to about 45 degrees in said azimuth direction with respect to the normal of the surface of said inspection object.

19. A surface inspection apparatus according to claim 12, wherein said illumination device forms a plurality of illumination spots on the surface of said inspection object with predetermined gasp among them, and said illumination device has a plurality of light reception sections capable of detecting individually said plurality of illumination spot images.

20. A surface inspection apparatus according to claim 11, wherein said illumination spot formed for each azimuth is individually detected by a plurality of optical detectors or an optical detector having a plurality of light reception sections and is converted to an electric signal.

21. A surface inspection apparatus according to claim 11, wherein said detection device has a plurality of optical detectors or an optical detector having a plurality of light reception sections, and the image of said illumination spot formed for each azimuth is individually detected.

22. A surface inspection apparatus according to claim 21, wherein said detection device has a single optical detector capable of collectively receiving images of said illumination spots formed for each of said azimuths, and utilizes said optical detector having said plurality of light reception sections and said single optical detector capable of collectively receiving light by switching both of said optical detectors.

23. A surface inspection apparatus according to claim 11, wherein the predetermined positional relationship comprises the same azimuth angle.

24. An azimuth scarred light image formation optical apparatus for a surface inspection apparatus for detecting foreign matters and defects existing on a surface of an inspection object or in the proximity of, and inside, the surface, on the basis of light detected by detection device, including an inspection object movement stage on which an inspection object is put and which moves said inspection object, illumination device that irradiates light to a predetermined position on a surface of said inspection object and forming an illumination spot and said detection device that detects light scattered, diffracted and reflected from said illumination spot, comprising:

a plurality of condensation concave mirrors arranged at a plurality of azimuth angles, respectively, with respect to the surface of said inspection object, and condensing and reflecting light scattered, diffracted and reflected from said illumination spot; and a plurality of image formation concave mirrors arranged at a higher angle of elevation than said condensation concave mirror with respect to the surface of said inspection object at each of said plurality of azimuth angles, and reflecting light reflected from each of said condensation concave mirrors arranged at a predetermined positional relationships with each of the plurality of image formation concave mirrors.

25. An azimuth scarred light image formation optical apparatus according to claim 24, wherein the predetermined positional relationship comprises the same azimuth angle.

* * * * *